United States Patent
Hakalehto

(10) Patent No.: US 9,493,797 B2
(45) Date of Patent: Nov. 15, 2016

(54) METHOD AND APPARATUS FOR ACCELERATING BIOTECHNICAL REACTION AND PRODUCTION

(71) Applicant: Eino Elias Hakalehto, Kuopio (FI)

(72) Inventor: Eino Elias Hakalehto, Kuopio (FI)

( * ) Notice: Subject to any disclaimer, the term of this patent is extended or adjusted under 35 U.S.C. 154(b) by 72 days.

(21) Appl. No.: 14/681,259

(22) Filed: Apr. 8, 2015

(65) Prior Publication Data

US 2015/0211027 A1    Jul. 30, 2015

Related U.S. Application Data

(62) Division of application No. 13/583,906, filed as application No. PCT/FI2011/000016 on Mar. 9, 2011, now Pat. No. 9,029,125.

(51) Int. Cl.
*C12P 7/18* (2006.01)
*C12M 1/00* (2006.01)
*C12P 7/16* (2006.01)
*C12P 39/00* (2006.01)

(52) U.S. Cl.
CPC ............. *C12P 7/18* (2013.01); *C12M 21/12* (2013.01); *C12M 23/02* (2013.01); *C12P 7/16* (2013.01); *C12P 39/00* (2013.01); *Y02E 50/10* (2013.01); *Y02E 50/343* (2013.01)

(58) Field of Classification Search
CPC ........ C12M 21/12; C12M 23/02; C12P 7/16; C12P 7/18; C12P 39/00; Y02E 50/10; Y02E 50/343
USPC ................. 435/158, 161, 167, 168
See application file for complete search history.

(56) References Cited

U.S. PATENT DOCUMENTS

| | | | | |
|---|---|---|---|---|
| 5,657,589 A | * | 8/1997 | De Bood | E04H 4/065 4/496 |
| 6,281,001 B1 | * | 8/2001 | McNelly | C05F 17/0072 210/612 |
| 6,284,528 B1 | * | 9/2001 | Wright | C05F 17/02 435/290.2 |
| 7,462,287 B2 | * | 12/2008 | Berrak | C02F 1/463 204/665 |
| 2001/0051371 A1 | * | 12/2001 | Kiplinger | C12M 23/02 435/262 |

FOREIGN PATENT DOCUMENTS

WO    WO 2007/142664    * 12/2007

OTHER PUBLICATIONS

Dusting et al. Flows Within a Cylindrical Cell Culture Bioreactor with a Free-Surface and a Rotating Base. 15th Australasian Fluid Mechanics Conference (2004), 4 pages.*

* cited by examiner

*Primary Examiner* — Scott Long
*Assistant Examiner* — Sean C Barron
(74) *Attorney, Agent, or Firm* — David Guerra

(57) ABSTRACT

The present invention is related to a method of using an apparatus for biotechnical production. The method includes the receiving a flow of an amount of a raw material into a basin. The basin has a radius, and a circular or sectorial configuration. A speed of the flow is increased towards a center of the basin. Followed by, introducing a gas to the flow of the raw material at an active site of the basin to create predetermined conditions that take place in the active site. The location is adjacent the center. A reaction broth is created at the location by reacting the flow with the gas. The reaction broth is moved to and past the active site using a belt located in the basin. The belt has a first section angled upwardly toward the center of the basin.

14 Claims, 3 Drawing Sheets

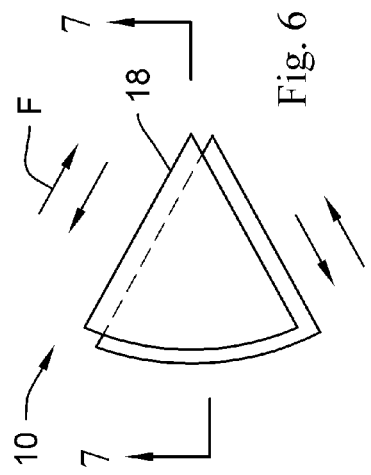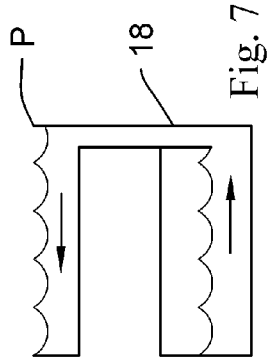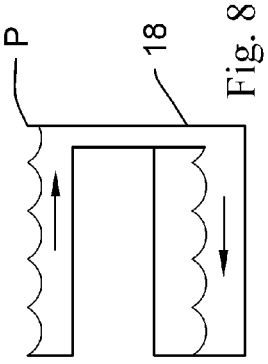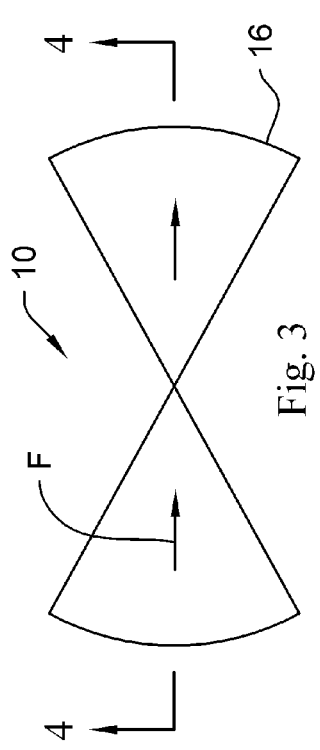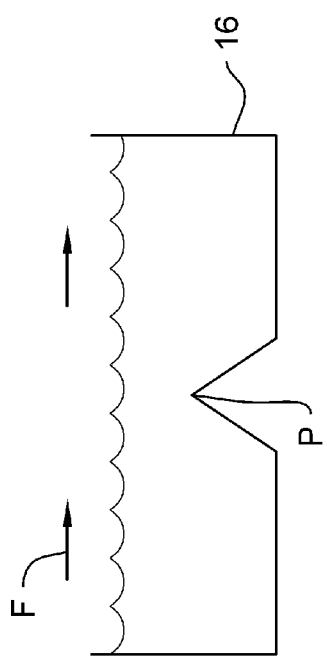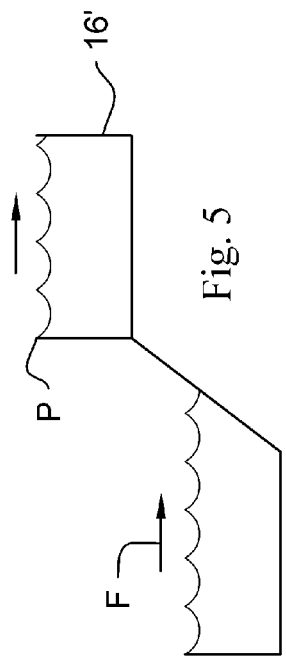

METHOD AND APPARATUS FOR ACCELERATING BIOTECHNICAL REACTION AND PRODUCTION

CROSS-REFERENCE TO RELATED APPLICATION

This application is a divisional application under 35 U.S.C. §121 and 37 CFR 1.53(b) based upon co-pending U.S. application Ser. No. 13/583,906 filed Sep. 10, 2012, which is a national phase application under 35 U.S.C. §371 based upon International Application No. PCT/FI2011/000016 filed on Mar. 9, 2011. Additionally, this divisional application claims the benefit of priority of co-pending U.S. application Ser. No. 13/583,906 filed Sep. 10, 2012. The entire disclosures of the prior applications are incorporated herein by reference.

BACKGROUND OF THE INVENTION

The present invention relates to a method and apparatus for accelerating biotechnical reaction and production for use in connection with increasing the ecological efficiency of energy production.

Biotechnological production processes, used to produce fuels and chemicals from organic starting materials, biomasses, are called biorefinement. Today's oil refineries, in fact, are based on the chemical methods, which were in use for biomass processing since the 1800s. Also involved is the strong development of microbiology starting in the mid-1800s, which has significantly contributed to our understanding of, among other things, naturally occurring degradation processes; they occur because of living organisms invisible to the naked eye. Some of these organisms are able to convert biomass degradation products to economically useful products, which can not only be utilized for energy production, but also as feedstock in various industrial chemical processes.

There have been extended periods, particularly after World War II during which crude oil and other fossil fuels were relatively inexpensive. The so-called petrochemical industry, which produces the chemical fractions that act as fuel and feedstock for other processes, is built upon these inexpensive raw materials. Burning fossil fuels has in turn led to environmentally damaging developments, such as acid rain, greenhouse gases, and possibly climate change. Energy crises have shown the vulnerability of the crude oil based economic system in situations where the price of oil has rapidly increased, or the availability of fossil fuels has otherwise been compromised by, for example, crises or varying political agendas. It is therefore very prudent to develop bioprocess solutions, based on inexpensive biomass such as waste materials. The processing of waste materials also contributes to the formation of environmental protection solutions within the economic system. The waste used can also be gaseous.

The metabolic reactions of micro-organisms essentially often release chemical energy from organic material. For this reason, the external energy consumption of microbial processes is usually low and the energy balance positive. This, and the fact that with biotechnical processes the same equipment can be used to carry out different reactions from variable raw materials, should be utilized as well as possible. Likewise, the thermal energy in gases can be utilized by committing it to the process. Similarly, the compounds in the gas can be made to react with the compounds in the process bath. This type of reaction can occur catalyzed by microbes and their enzymes. At the same time the environmental load of emissions from combustion plants are reduced.

Microbial metabolic reactions are mainly anabolic, related to the construction of cells, and catabolic i.e. cell energy usage. In some circumstances, microbes are content to just process the molecules in the environment, in order to change the conditions to be beneficial or to keep existing beneficial circumstances in place. These reactions may also contain symbiotic interactions between microbes. Sometimes bacterial cells consume more chemical energy than they need. The energy is then either stored in the cells, or bound to the large quantity of synthesized product without causing significant cell growth (cell division). This is often referred to as overflow metabolism.

Overflow metabolism is a verified phenomenon in the metabolism of many bacteria. It's not really a catabolic or an anabolic reaction. Bacteria using overflow metabolism neither use the chemical energy released in this reaction for their own needs, nor build new cell growth on this metabolism. In terms of the bacterial population the main purpose of overflow metabolism is to change the environment so that the conditions necessary for life are maintained or improved. Overflow metabolism occurs especially when abundant carbon and energy sources are available. Through this action, bacteria are trying to compete with other microbes, e.g. by consuming the extra nutrients so that they're out of the reach of competitors.

Since overflow metabolism is not related to bacterial growth, its regulatory mechanisms may differ from normal metabolic regulation, and remain largely unknown. The research has also been limited by the fact that, in terms of bacteria, they often represent extreme or atypical conditions. These reactions clearly play an important part in the circulation of matter in nature as a part of microbial metabolism. Thus, these reactions can be made use of industrially, for example in fuel or chemical production. Similarly they can be used to convert gaseous compounds to a liquid or solid phase.

Microbial metabolism is usually divided into energy-producing respiratory or fermentation (catabolic), and anabolic cell building-related reactions. At the cellular level, these reactions usually occur simultaneously. Additionally, microbial survival under different conditions may also be associated with other reactions, such as the emergence of highly durable forms (egg, bacterial spores) or overflow metabolism. The purpose of these reactions is to enable the survival of the bacterial population. Their industrial exploitation has not yet been specifically explored, although they may involve significantly rapid substance transitions or reactions.

When the microbial population is introduced to favorable circumstances, it generally moves to the active growth phase (exponential growth). It is preceded by the so-called lag phase, during which the population cells synthesize the enzymes and other molecules necessary for growth, and are thus "restocked." Growth stage may be a multi-tiered, due, for example, to the tendency of microbes to first use up one main carbon and energy source from their substrate, and then move on to other sources. (e.g. secondary metabolism). Often this requires the synthesis of new enzymes, including hydrolytic.

Under natural conditions (non laboratory), microbes often occur in mixed populations. Their activities involve various interactions, such as commensalism. As an example, the pH control of the beginning of the small intestines has been linked to the co-operation of facultatively anaerobic bacteria (Hakalehto, 2008). Changes in gut flora will also affect the life of the host organism. Concerning obesity, it has been established that individuals with a tendency towards obesity have a greater concentration of butyrate producing bacteria in the first part of the colon.

For example, 2,3-butanediol production takes place in the intestinal tract in a much earlier stage; namely in the duodenum and the rest of the small intestine. The human body absorbs 80% of its nutrients in those regions. Rapid use of nutrients by the host as well as by the microbial flora is particularly fast, and therefore thick biofilms, such as in the colon, cannot form on the intestinal walls. Other anaerobic metabolic reactions include, for example: acetone-butanol fermentation, ethanol fermentation, methane fermentation and production of several organic acids.

The bacteria active within flora of the beginning of the small intestines, including the duodenum, consist particularly of those being highly bile resistant and commensalistically capable, even in those circumstances (Hakalehto et al, 2010). Additionally, under these circumstances because of the actions of, among others, *Klebsiella* sp. and *Enterobacter* sp. genera of bacteria, ethanol and 2,3-butanediol are formed. Thus, by exploring these intestinal conditions it is possible to learn useful things pertaining to the industrial production of these chemicals. The important thing is that the active microbes collaborate with many other microbial components, such as the *Escherichia coli*. A method for efficient culturing of these bacteria is presented in the Example 1. The pH drop caused by the organic acids produced by *E. coli* and other bacteria carrying out mixed acid fermentation is balanced by the neutral components, ethanol and 2,3 butanediol, produced by *Klebsiella* and *Enterobacter* group of bacteria. In all of these and most other bacterial metabolic reactions differing amounts of carbon dioxide, $CO_2$, are released. If the carbon dioxide that was produced in the reaction or otherwise introduced to the process can be made to react or otherwise combine with the process bath, the amount of $CO_2$ released is reduced. If the $CO_2$ or carbon monoxide is a product of combustion or incineration and its release into the atmosphere when introduced to the bio-process is reduced as described above, then the general environmental burden and environmental impact of the specific combustion or incineration is lessened.

Therefore, a need exists for a new and improved method and apparatus for accelerating biotechnical reaction and production that can be used for increasing the ecological efficiency of energy production. In this regard, the present invention substantially fulfills this need. In this respect, the method and apparatus for accelerating biotechnical reaction and production according to the present invention substantially departs from the conventional concepts and designs of the prior art, and in doing so provides an apparatus primarily developed for the purpose of increasing the ecological efficiency of energy production.

BRIEF SUMMARY OF THE INVENTION

In view of the foregoing disadvantages inherent in the known types of biotechnological production processes now present in the prior art, the present invention provides an improved method for accelerating biotechnical reaction and production, and overcomes the above-mentioned disadvantages and drawbacks of the prior art. As such, the general purpose of the present invention, which will be described subsequently in greater detail, is to provide a new and improved method for accelerating biotechnical reaction and production and method which has all the advantages of the prior art mentioned heretofore and many novel features that result in a method for accelerating biotechnical reaction and production which is not anticipated, rendered obvious, suggested, or even implied by the prior art, either alone or in any combination thereof.

To attain this, the present invention essentially comprises a biotechnical production method of creating ideal conditions that take place in at least one location within a core of a bioreactor. The location a reaction occurs is as close to an optimal level as possible and despite a rapid flow of a reaction bath a high productivity achieved through the conditions enables abundant product formation.

The present invention is related to a method of biotechnical production using an apparatus. The method includes receiving a flow of an amount of a raw material into a basin. The basin has a radius, and a circular or sectorial configuration. A speed of the flow is increased towards a center of the basin. Followed by, introducing a gas to the flow of the raw material at an active site of the basin to create predetermined conditions that take place in the active site. The location is adjacent the center. A reaction broth is created at the location by reacting the flow with the gas. The reaction broth is moved to and past the active site using a belt located in the basin. The belt has a first section angled upwardly toward the center of the basin.

There has thus been outlined, rather broadly, the more important features of the invention in order that the detailed description thereof that follows may be better understood and in order that the present contribution to the art may be better appreciated.

The invention may also include steps of binding the gas in part with the reaction broth after being formed in a combustion reaction, or introducing at least one substance to the reaction broth, with the substance is selected from the group consisting of nutrients, growth factors, precursors, regulatory factors, microbes and microbial cultures. There are, of course, additional features of the invention that will be described hereinafter and which will form the subject matter of the claims attached.

Another aspect of the invention may also include the step of producing at least one product from the production reaction, with the product being selected from the group consisting of ethanol, 2,3-butanediol, and organic chemicals. The product may then be exploited as one of fuels, hydrogen, methane, and other gases suitable for energy production.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved method for accelerating biotechnical reaction and production that has all of the advantages of the prior art biotechnological production processes and none of the disadvantages.

It is another object of the present invention to provide a new and improved method for accelerating biotechnical reaction and production that may be easily and efficiently manufactured and marketed.

An even further object of the present invention is to provide a new and improved method for accelerating biotechnical reaction and production that has a low cost of manufacture with regard to both materials and labor, and which accordingly is then susceptible of low prices of sale to the consuming public, thereby making such method for accelerating biotechnical reaction and production economically available to the buying public.

Still another object of the present invention is to provide a new method for accelerating biotechnical reaction and production that provides in the apparatuses and methods of the prior art some of the advantages thereof, while simultaneously overcoming some of the disadvantages normally associated therewith.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a planar view of an embodiment of the sectorial basin of the present invention.

FIG. 4 is a cross-sectional view of the sectorial basin taken along line 4-4 in FIG. 3.

FIG. 5 is a cross-sectional view of an alternate embodiment of the sectorial basin of FIG. 3.

FIG. 6 is a perspective view of an embodiment of the sectorial basin of the present invention.

FIG. 7 is a cross-sectional view of the alternate embodiment of the sectorial basin taken along line 7-7 in FIG. 6.

FIG. 8 is a cross-sectional view of the alternate embodiment of the sectorial basin of FIG. 6 showing a revers flow.

The same reference numerals refer to the same parts throughout the various figures.

DETAILED DESCRIPTION OF THE INVENTION

With the invented method and apparatus it is possible to:
1. Transform multiple biomass based waste materials to valuable raw materials enabling their recycling.
2. Reduce the greenhouse gas emissions of manufacturing biotechnical chemicals and fuels.
3. Bind the carbon molecules present in biomass to products and commodities such as durable plastic or rubber-based materials (if they are not consumer goods the carbon emissions can be bound to the material for a long time).
4. Utilize the chemical energy released from waste without a net increase in $CO_2$ emissions in energy production. Also, the released $CO_2$ can be bound to a under glass plant or algae material (tissue).

In the light of the aforementioned benefits it is easy to see how a method using this invention can significantly increase the ecological efficiency of the chemical industry and energy production. This method according to the present invention and the device based on it can be used for producing gasoline equivalent butanol, or ethanol as a fuel for internal combustion engines.

Similarly, 2,3-butanediol, acetone, organic acids or other compounds can be produced as raw materials for the chemical industry or gases such as methane or hydrogen, for energy production. At the same time one product of the process is reduced organic waste and environmental load. As seen in the Example 2, the volume of gases like $CO_2$ can be reduced using methods detailed by this invention and consequently the amount of greenhouse gases is reduced. In this way carbon can be bound to different plastics or synthetic rubbers, which can be used in various long lived purposes like for road surface materials.

Figure 1:
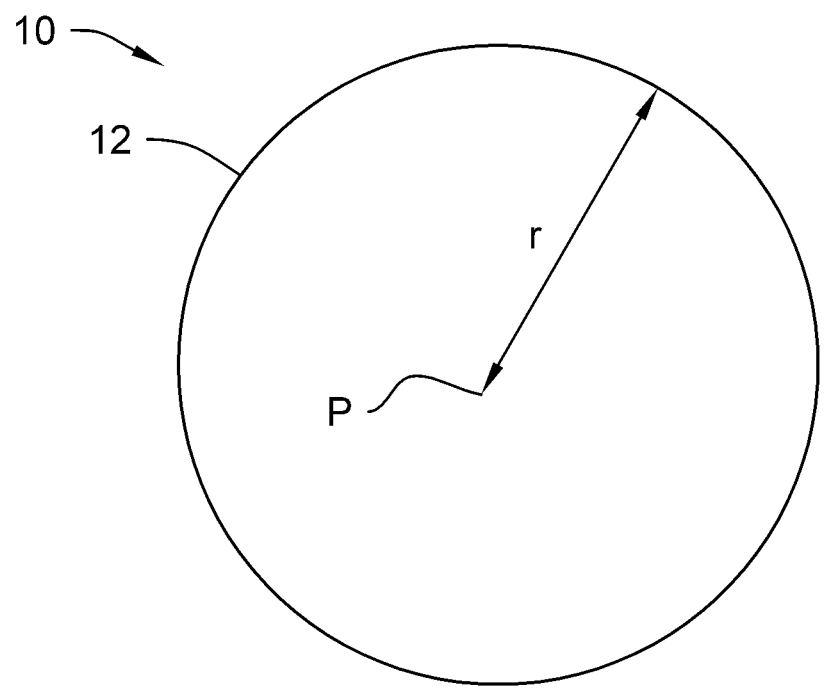
FIG. 1 is a planar view of an embodiment of the basin of the method and apparatus for accelerating biotechnical reaction and production constructed in accordance with the principles of the present invention.
Figure 2:
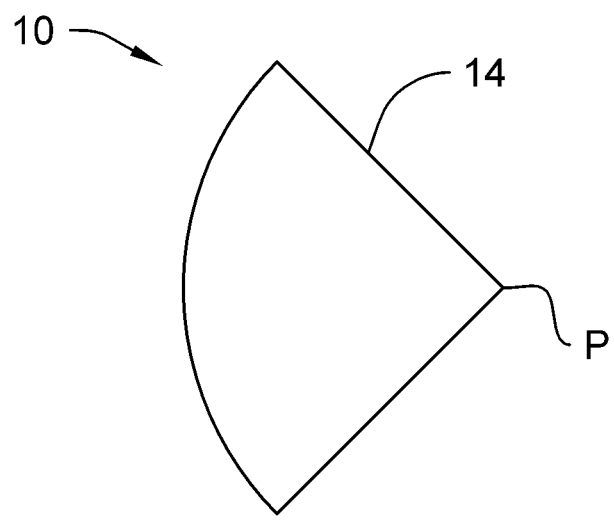
FIG. 2 is a planar view of the sectorial basin of the present invention.

A common problem with biotechnical reactions is diffusion limitations. This means that substances necessary for microbe nutrition or product formation do not reach the microbes or other biocatalysts quickly enough, and respectively waste products don't leave fast enough. With the presently invented method and apparatus gas is added to the active site to speed up diffusion. The diffusion problem is lessened due to the sped up production reaction or its main parts taking place within the limited space of a small part of the reactor. In this way, the physical conditions such as temperature or pH, can be adjusted for optimal product formation. Bioreactor 10 itself can be implemented with a circular basin 12 (FIG. 1) with a center P of a radius r, a sectorial basin 14, 16, 16', 18 (FIGS. 2-8) with a center P, or in the shape of the pool 20, 22 (FIG. 9) or with belt 24 (FIG. 10).

All the reactions taking place in bioreactor 10 can be measured and regulated through the central unit, which in turn can be controlled remotely. In this way, the bioreactor 10 can operate automatically but is still under constant surveillance.

In order to obtain ideal diffusion conditions for the formation of a biotechnical product the invented method and apparatus injects the heart of bioreactor 10 ("active site") with the necessary additions. These may include gas flow, or other additions maintaining favorable conditions, such as by injecting gaseous substances to sustain optimal production temperature in order to create ideal reaction conditions. Liquids or suspensions, may also be added. Added substances or materials may be different nutrients, growth factors, raw materials, regulatory factors, microbial cultures or any other substrates or microbes useful for production. In this patent application, substrate means a gas, liquid or solid substance added to the reaction, reaction broth and the active site which takes part in the reaction or its regulation. Reaction broth or process bath, or broth stands for the entire main portion of the substances taking part in the reaction, which can be inoculated with production microbes or enzymes, or it can be uninoculated. The bath or broth may contain the naturally occurring microbes of its biomass raw materials.

At this point it's usually possible raise the flow speed F of the bath or broth quite high due to high productivity. Similarly, pretreatments, such as enzymatic or other hydrolytic reactions or microbial growth, are slower and so call for slower flow speeds and higher volumes. One of the core ideas of this present invented method and apparatus, is to concentrate the conditions necessary for high reaction speed into the heart of the bioreactor 10. This may include, for example, pH adjustment, as well as the adding in of various nutrients and regulatory substances, or other substances. Various control measures may also be implemented through the addition of gaseous substances, for example, the beginning of *Escherichia coli* growth, can be accelerated by adding carbon dioxide (Hakalehto, 2011). If combustion fumes containing carbon dioxide and/or carbon monoxide are led into the bioreactor, these gases and the carbon they contain can contribute to the formation of reaction product, as shown in Example 2. The carbon sequestration can then be used to reduce the climate impact of the combustion gases and to restore carbon bound in the bioreactor to a liquid and/or solid state.

In the same way as in the different phases of biomass pretreatment or microbe propagation i.e. culturing, the aftertreatment can also include the handling of growing volumes when compared to the production reaction action site in the core of the bioreactor. The speed of the process can also be adjusted by adjusting the flow rate. Not only the reaction bath flow, but also the flow rate of different substance additions and the pH and temperature can be regulated. To facilitate adjustments it is essential that chemical sensors be installed in varying locations in the bioreactor to measure physical or biological parameters.

Figure 9:
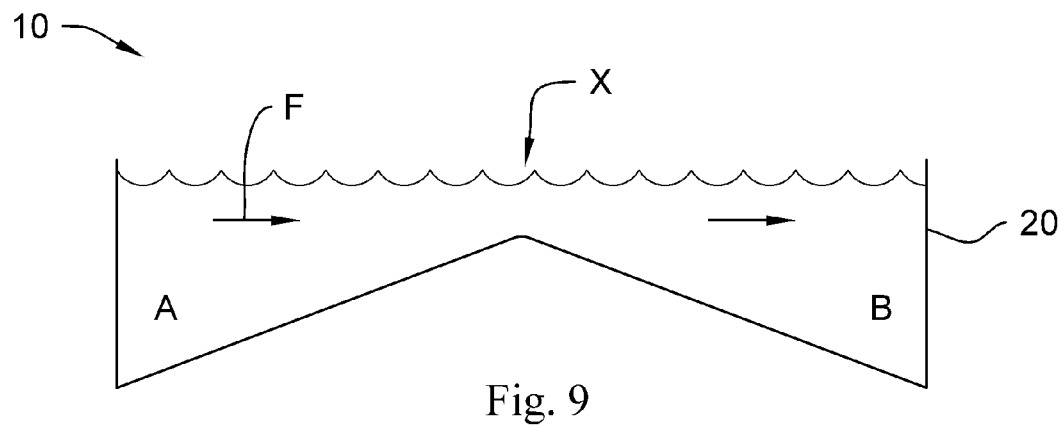
FIG. 9 is a cross-sectional view of an alternate embodiment of the sectorial basin.
Figure 10:
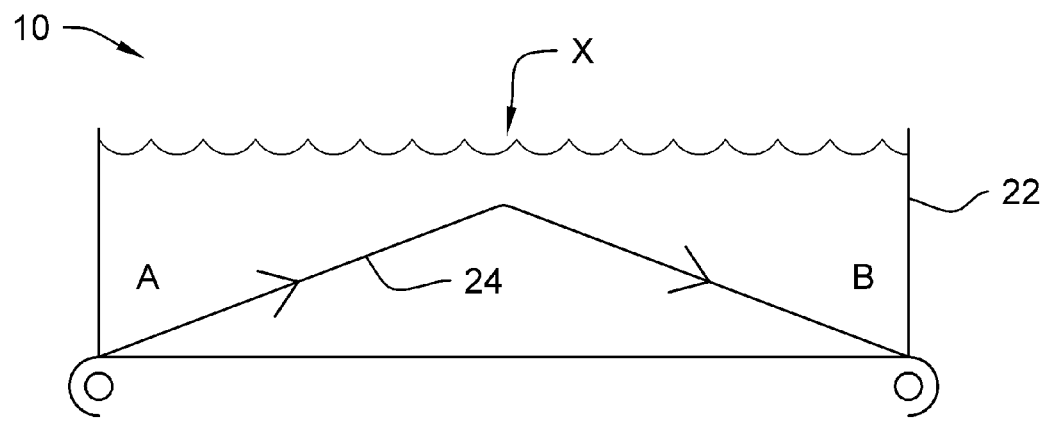
FIG. 10 is a cross-sectional view of an alternate embodiment of the sectorial basin featuring the belt.

The bioreactor can be implemented in a flow pool 20, 22 with depth variations (FIGS. 9 and 10). Then in both cases, the reactor volume is at its lowest in the bioreactor core in (x), and it is to this point that the necessary additions for accelerating the reaction are added. These may include microbe addition. All additions can be achieved, for example by bubbling, spraying, injecting, pouring, or other equivalent means. Pre-treatment is carried out in Part A, after-treatment in Part B. The corresponding markings have been made to the figure where the reactors A- and B-parts are both sector-shaped. The total volume can be adjusted by moving the sector side walls, and thus enlarging the scope of sector or a reduction. Basin-shaped reactor volume can be adjusted by changing the height of the running belt 24. Flow basin 22 and the belt 24 can of course be placed in a tube. In this case, biotechnical process and production can be either partially or fully implement during the process-, i.e. reaction-bath transport.

Example 1

Growing Bacteria in a PMEU Device (Portable Microbe Enrichment Unit)

Inoculating bacterial culture propagated overnight in THG-nutrient broth tubes (tryptone-yeast extract-glucose) to the corresponding substrate in a PMEU-cultivation syringe. This is transferred to a PMEU (Portable Microbe Enrichment Unit) growing device suitable growth temperature. With *E. coli* and *K. mobilis*-bacteria, this temperature may be +35 or +37° C. Culturing is carried out as described previously: aerobically, anaerobically or microaerobically (Hakalehto et al, 2008).

Example 2

*Klebsiella mobilis* and *Escherichia coli* mixed cultures in microaerobic conditions of +37° C. yielded two isomers of 2,3-butanediol, as seen in Table 1. K-culture is grown in a THG (tryptone-yeast extract-glucose) substrate containing 20% enzymatically hydrolyzed sawdust, while the KS cultures also contained 10% of enzymatically hydrolyzed cellulose. Acetate (0.1%) was added to 9.5 hours after incubation and additional THG substrate after 11.5 hours, when the pH was adjusted to 6.5. Microbial cultures were added at the same time point (5% *K. mobilis* and 5% of *E. coli* culture), and 3 ml cellulase enzyme solution. Container volume was 81, which reflects the bioreactor production points, i.e. the points to which the necessary additions are made. When the incubation had lasted 36 and 47 hours, 4 ml and 3 ml, respectively, of cellulase enzyme was added. K-cultures began an intense gas formation at 17.5 hour's time, which gas presumably consisted mainly of carbon dioxide. However, bubbling, was almost non-existent in the KS culture, which contained more cellulose derived glucose (197 mg/dl in the beginning of the reaction versus the 36 mg/dl glucose levels of the K-culture). Thus, the overflow metabolism realized in the KS-culture resulted in increased production of 2,3-butanediol, which can be seen in Table 1, without high gas e.g. carbon dioxide production or emission. The fact that this is mainly overflow metabolism is seen in Table 2. It is assumed that carbon dioxide formed in bacterial respiration, or the fermentative reactions in KS culture, was utilized as a part of the cultures metabolism.

LITERATURE

E. Hakalehto, T. Humppi, H. Paakkanen, Dualistic acidic and neutral glucose fermentation balance in small intestine: Simulation in vitro. *Pathophysiology* (2008)

E. Hakalehto, M. Hell, C. Bernhofer, A. Heitto, J. Pesola, T. Humppi, H. Paakkanen, Growth and gaseous emissions of pure and mixed small intestinal bacterial cultures in PMEU: Effects of bile and vancomycin. *Pathophysiology* (2010)

E. Hakalehto, Simulation of enhanced growth and metabolism of intestinal *Escherichia coli* in the Portable Microbe Enrichment Unit (PMEU). M. C. Rogers and N. D. Peterson (Eds.), *E. coli* interactions: causes, treatment and prevention. Nova Publishers, New York, USA. In Press.

TABLE 1

The amount of 2,3-butanediol formed by the mixed culture of
Klebsiella mobilis and Escherichia coli (K) in proportion
to the butanediol production levels in the KS-culture as percentages.
Description of the conditions in the text part of the Example
2. The elevated butanediol production is combined with reduced
gas emissions in the reaction.

| Time Point (h) | KS/2,3-butanediol isomer 1 | K/2,3-butanediol isomer 1 | KS/2,3-butanediol isomer 2 | K/2,3-butanediol isomer 2 | 2,3-butanediol (K/KS) |
|---|---|---|---|---|---|
| 0 | 0 | 0 | 0 | 18.20 | — |
| 4.5 | 57.43 | 0 | 29.31 | 18.65 | 21.5% |
| 7.5 | 67.71 | 0 | 56.72 | 21.74 | 17.5% |
| 10.5 | 56.34 | 0 | 58.59 | 43.26 | 38.8% |
| 14.5 | 0 | 57.88 | 46.26 | 40.81 | 213.3% |
| 16.5 | 55.51 | 59.54 | 197.11 | 43.31 | 40.7% |
| 17.5 | 76.92 | 57.01 | 90.14 | 52.66 | 66.4% |
| 21.5 | 94.15 | 60.27 | 108.98 | 57.56 | 58.0% |
| 24.5 | 101.46 | 66.72 | 99.93 | 48.24 | 57.1% |
| 27 | 133.84 | 76.17 | 94.46 | 53.22 | 56.7% |
| 28 | 195.89 | 70.58 | 130.16 | 43.79 | 35.1% |
| 29.5 | 213.99 | 99.86 | 182.53 | 63.59 | 41.2% |
| 34 | 248.99 | 109.44 | 135.74 | 57.52 | 50.9% |
| 46.5 | 289.53 | 147.76 | 147.58 | 54.11 | 46.2% |
| 49.5 | 248.05 | 152.16 | 145.26 | 45.66 | 50.3% |
| 51.5 | 326.95 | 99.16 | 204.75 | 53.38 | 28.7% |
| 54 | 345.36 | 129.70 | 174.53 | 53.34 | 35.2% |

TABLE 2

The bacterial concentrations of the K- and KS cultures (cfu, colony
forming units) in a milliliter at time point 253 hours, when they contained
10-fold difference as determined by TYG-agar. This implies to increased
2,3-butanediol production being not related to the anabolic reactions
in the cultures but to the overflow metabolism.

| Culture | bacterial concentration | |
|---|---|---|
| | K | KS |
| E. coli | 3 × 10 exp 7 | 2.4 × 10 exp 8 |
| K. mobilis | 6 × 10 exp 7 | 2.5 10 exp 8 |

What is claimed as being new and desired to be protected by Letters Patent of the United States is as follows:

1. A method of producing a biotechnical production, said method comprising the steps of:
   a) receiving a flow of an amount of a raw material into a basin, said basin having a radius, and a configuration selected from the group consisting of circular, and sectorial;
   b) increasing a speed of said flow towards a center of said basin;
   c) introducing a gas to said flow of said raw material in at least one location of an active site of said basin to create predetermined conditions that take place in said active site, said location being adjacent said center;
   d) creating a reaction broth at said location by reacting said flow with said gas; and
   e) moving said reaction broth to and past said active site using a belt located in said basin, said belt having a first section angled upwardly toward said center of said basin.

2. The method in accordance with claim 1, wherein said gas is introduced to said location even if conditions in other parts of said basin are different than said predetermined conditions in said active site.

3. The method in accordance with claim 2, wherein said gas contains at least one of carbon dioxide, carbon dioxide and monoxide, and carbon monoxide.

4. The method in accordance with claim 3 further comprising the step of binding said gas in part with said reaction broth after being formed in a combustion reaction.

5. The in accordance with claim 4 further comprising the step of introducing at least one substance to said reaction broth, said substance is selected from the group consisting of nutrients, growth factors, precursors, regulatory factors, microbes and microbial cultures.

6. The method in accordance with claim 5, wherein a production reaction carried out by said substance is an overflow reaction.

7. The method in accordance with claim 6 further comprising the step of producing at least one product from said production reaction, said product being selected from the group consisting of ethanol, 2,3-butanediol, and organic chemicals.

8. The method in accordance with claim 7 further comprising the step of exploiting industrially said product as one of fuels, hydrogen, methane, and gases suitable for energy production.

9. The method in accordance with claim 1 further comprising the step of measuring and regulating, by a central unit, at least one reaction in said basin.

10. The method in accordance with claim 1 further comprising the step, prior to step b), of pretreating said flow.

11. The method in accordance with claim 1, wherein said basin as a volume with varying depth, and wherein a depth at said center is less than a depth at a second location of said basin.

12. The method in accordance with claim 11 further comprising the step of adjusting said volume of said basin by changing a height of said belt.

13. The method in accordance with claim 11 further comprising the step of adjusting said volume of said basin by moving at least one basin sidewall.

14. The method in accordance with claim 1, where said basin and said belt are located in a tube.

* * * * *